US005900227A

United States Patent [19]
Janzen et al.

[11] Patent Number: 5,900,227
[45] Date of Patent: May 4, 1999

[54] MULTICYCLIC NITRONE SPIN TRAPPING COMPOSITIONS

[75] Inventors: Edward G. Janzen; Nagaraju Sankuratri, both of Oklahoma City, Okla.

[73] Assignee: Oklahoma Medical Research Foundation, Oklahoma City, Okla.

[21] Appl. No.: 08/664,450

[22] Filed: Jun. 17, 1996

[51] Int. Cl.$^6$ .......................... A61K 49/00; G01N 31/00; G01N 33/48
[52] U.S. Cl. .......................... 424/9.33; 540/450; 540/451
[58] Field of Search .................................. 424/1.11, 1.65, 424/9.3, 9.33; 514/79, 83; 540/1, 450, 451, 454, 455, 456

[56] References Cited

U.S. PATENT DOCUMENTS

| | | |
|---|---|---|
| 3,296,145 | 1/1967 | Findlam et al. . |
| 3,849,934 | 11/1974 | Dorschner et al. . |
| 4,153,722 | 5/1979 | Campbell et al. . |
| 4,197,314 | 4/1980 | Campbell et al. . |
| 4,214,003 | 7/1980 | Campbell et al. . |
| 4,216,231 | 8/1980 | Tanida . |
| 4,224,340 | 9/1980 | Campbell et al. . |
| 4,870,002 | 9/1989 | Kiel . |
| 5,036,097 | 7/1991 | Floyd et al. . |
| 5,681,845 | 10/1997 | Janzen et al. ............................ 514/424 |

FOREIGN PATENT DOCUMENTS

| | | |
|---|---|---|
| WO 88/05044 | 7/1988 | WIPO . |
| WO 88/05653 | 8/1988 | WIPO . |
| WO 91/05552 | 5/1991 | WIPO . |
| WO 92/22290 | 12/1992 | WIPO . |

OTHER PUBLICATIONS

Baethmann, et al., "Mediators of Brain Edema and Secondary Brain Damage", *Critical Care Medicine*, 16(10):972–977 (1988).
Bancroft, et al., "Spin Trapping with Covalently Immobilized α–Phenyl–N–[(1–hydroxy–2–methyl)–2–propyl] Nitrone", *J. Phys. Chem.*, 84(5):557–558 (1980).
Bapat & Black, "Nitrones and Oxaziridines, I. Preparation of I–Pyrroline I–Oxides and I–Pyrroline By Reductive Cyclization of γ–Nitro Carbonyl Compounds", *Aust. J. Chem.*, 21:2483–2495 (1968).
Barasch, et al., "Novel DMPO–Derived $^{13}$C–Labeled Spin Traps Yield Identifiable Stable Nitroxides", *J. Am. Chem. Soc.*, 116:7319–7324 (1994).
Black & Blackman, "Nitrones and Oxaziridines. XXV* Bromination of 2–t–Butyl– and 2–Phenyl–1–pyrroline 1–Oxides", *Aust. J. Chem.*, 32:1795–1803 (1979).
Black & Boscacci, "Nitrones and Oxaziridines, XV Approaches to 3–Oxo–I–Pyrroline I–Oxides by Oxidation of I–Pyrroline I–Oxides", *Aust. J. Chem.*, 29:3511 (1976).
Bolli & McCay, "Use of Spin Traps in Intact Animals Undergoing Myocardial Ischemia/Reperfusion: A New Approach to Assessing the Role of Oxygen Radicals in Myocardial 'Stunning'," *Free Rad. Res. Comms.*, 9(3–6):169–180 (1990).

Bolli, et al., "Demonstration of Free Radical Generation in "Stunned" Myocardium of Intact Dogs with the Use of the Spin Trap α–Phenyl N–Tert–Butyl Nitrone", *J. Clin. Invest.*, 82:476–485 (1988).
Bonnett, et al., "Experiments Towards the Synthesis of Corrins, Part II, The Preparation and Reactions of I–Pyrroline 1–Oxides", *J. Chem. Soc.*, 2094–2102 (1959).
Buettner & Oberly, "Considerations in the Spin Trapping of Superoxide and Hydroxyl Radical in Aqueous Systems Using 5,5–Dimethyl–I–pyrroline–I–oxide", *Biochem. Biophys. Res. Com.*, 83:69 (1978).
Buettner, "The Syringe Nitroxide Free Radical–Part II", *Free Rad. Res. Commun.*, 19(S1):S228–S230 (1993).
Carney, et al., "Protection Against Oxidative Damage to CNS by α–Phenyl–tert–Butyl Nitrone (PBN) and Other Spin–Trapping Agents: A Novel Series of Nonlipid Free Radical Scavengers" *J. Mol. Neurosci.*, 3:47–57(1990).
Carney, et al., "Reversal of Age–related Increase in Brain Protein Oxidation, Decrease in Enzyme Activity, and Loss in Temporal and Spatial Memory by Chronic Administration of the Spin–Trapping Compound N–tert–Butyl–α–Phenylnitrone", *Proc. Natl. Acad. Sci. USA*, 88:3633–3636 (1991).
Chandler, et al., "An Unanesthetized–Gerbil Model of Cerebral Ischemia–induced Behavioral Changes", *J. Pharm. Methods*, 14:137–146 (1985).
Chen, et al., "Excretion, Metabolism and Tissue Distribution of a Spin–Trapping Agent, α–Phenyl–N–Tert–Butyl–Nitrone (PBN in Rats," *Free Rad. Res. Comms.*, 9(3–6):317–323 (1990).
Chiu, et al, "Effect of Catalase and/or Allopurinol, or N–t–Butyl–α–Phenylnitrone on Hepatic Ischemia", *Transplantation Proceedings*, XIX(I):1077–1079 (1987).
Curran, et al., "Viral and Cellular for Proteins Are Complexed with a 39,000–Dalton Cellular Protein", *Mol. Cell Biol.*, 5:167–172 (1985).
Degray & Mason, "Biological Spin Trapping", Electron Spin Resonance, Chapter 8, 246–319 (?).
Ernster, "Biochemistry of Reoxygenation Injury", *Critical Care Medicine*, 16(10):947–953 (1988).

(List continued on next page.)

*Primary Examiner*—John Kight
*Assistant Examiner*—Dameron Jones
*Attorney, Agent, or Firm*—Arnall Golden & Gregory, LLP

[57] ABSTRACT

Multicyclic nitrone spin trapping compounds capable of forming stable free radical spin adducts are provided as well as methods for their synthesis. The multicyclic nitrone spin trapping compounds can be reacted with a free radical, such as a hydroxy or hydroperoxy radical, in solution to form a spin adduct which is stable and readily detectable by electron paramagnetic resonance (EPR) spectroscopy. The multicyclic nitrone spin traps can be used to detect free radicals in a sample such as a biological system. In one embodiment, the spin trapping compound, 1,3,3-trimethyl-6-azabicyclo-[3.2.1]oct-6-ene-N-oxide ("TRAZON") is provided, as well as methods for the synthesis of TRAZON and of modified forms of TRAZON. TRAZON can react with a wide range of different free radicals in solution to form free radical spin adducts which are readily detectable by EPR.

22 Claims, 4 Drawing Sheets

OTHER PUBLICATIONS

Finkelstein, et al., "Spin Trapping. Kinetics of the Reaction of Superoxide and Hydroxyl Radicals with Nitrones", *J. Am. Chem. Soc.,* 102:4994–4999 (1980).

Finkelstein, et al., "Spin Trapping of Superoxide", *Mol. Pharmacol.,* 16:676 (1979).

Finkelstein, et al., Spin Trapping of Superoxide and Hydroxyl Radical: Practical Aspects[1], *Arch. Biochem. and Biophys.,* 200(1)1–16 (1980).

Floyd, et al., "Age Influence on Oxidative Events During Brain Ischemia/Reperfusion", *Arch. Gerontol. Geriatr.,* 12:155–177 (1991).

Frejaville, et al., "5–Diethoxyphosphoryl–5–methyl–1–pyrroline N–Oxide (DEPMPO): A New Phosphorylated Nitrone for the Efficient In Vitro and In Vivo Spin Trapping of Oxygen–centered Radicals", *J. Chem. Soc., Chem. Commun.,* 1793–1794 (1994).

Gelvan, et al., "Cardiac Reperfusion Damage Prevented by a Nitroxide Free Radical," *Proc. Natl. Acad. Sci. USA,* 88(11):4680–4684 (Jun. 1, 1991).

Giercksky, et al., "Epidemiology of NSAID–Related Gastrointestinal Side Effects," *Scand. J. Gastroenterology,* 3–7 (1989).

Haire, et al., "The First H and N ENDOR Spectra of An Oxygen–Centered Radical Adduct of DMPQ–type Nitrones", *Can. J. Chem.,* 66:7395 (1988).

Haire, et al., "A More Efficient Synthesis of DMPO–Type (Nitrone) Spin Traps", *J. Org. Chem.,* 51:4298–4300 (1986).

Haire, et al., "NMR Solvent Effect Study of Pyrroline–N–Oxide Spin Traps: Microenvironments in Sodium Dodecyl Sulfate Micelles", *Magnetic Res. Chemistry,* 33:1–7 (1995).

Haire & Janzen, "Synthesis and Spin Trapping Kinetics of New Alkyl Substituted Cyclic Nitrones", *Can. J. Chem.,* 60:1514–1522 (1982).

Hall, et al., "Correlation Between Attenuation of Postraumatic Spinal Cord Ischemia and Preservation of Tissue Vitamin E by the 21–Aminosteroid U74006E: Evidence for an In Vivo Antioxidant Mechanism", *J. of Neurotrauma,* 6(3):169–176 (1989).

Hall, "Free Radicals and CNS Injury" *Critical Care Clinics,* 5(4):793–805 (1989).

Halliwell & Gutteridge, Free Radicals in Biology and Medicine, Second Edition., Oxford, Clarendon Press, 1989.

Hamburger, et al., "Endotoxin–Induced Mortality in Rats is Reduced by Nitrones", *Circulatory Shock,* 29:329–334 (1989).

Harbour, et al., An Electron Spin Resonance Study of the Spin Adducts of OH and $HO_2$, *Can. J. Chem.,* 52:3549 (1974).

Hearse & Tosaki, "Reperfusion–Induced Arrhythmias and Free Radicals: Studies in the Rat Heart with DMPO," *J. Cardiovasc. Pharmacol.,* 9(6):641–650 (1987).

Hearse, et al., "Free Radicals and Reperfusion–Induced Arrhythmias: Protection by Spin Trap Agent PBN in the Rat Heart", *Circulation Research,* 60(3):375–383 (1987).

Hearse, et al., "Free Radicals and Calcium: Simultaneous Interacting Triggers as Determinants of Vulnerability to Reperfusion–Induced Arrhythmias in the Rat Heart" *J. Mol. Cell. Cardiol.,* 20:213–223 (1988).

Hillman & Bloom, "Economic Effects of Prophylactic Use of Misoprostol to Prevent Gastric Ulcer in Patients Taking Nonsteroidal Anti–inflammatory Drugs," *Arch. Intern. Med.* 149:2061–2065 (1989).

Hossman, "Resuscitation Potentials After Prolonged Global Cerebral Ischemia in Cats", *Critical Care Medicine,* 16(10):964–971 (1988).

Ilieva, et al., "Noradrenaline and Adrenaline in the Adrenal Glands and Myocardiun During Endotoxin Shock and Antioxidant Therapy", *Neurosciences,* 12:223–227 (1986) (abstract).

Janzen & Liu, "Radical Addition Reactions of 5,5–Dimethyl–1–pyrroline–1–oxide. ESR Spin Trapping with a Cyclic Nitrone", *Journal of Magnetic Resonance,* 9(3):510–512 (1973).

Janzen, et al., "Factors Influencing Hyperfine Splitting in the ESR Spectra of Five–Membered Ring Nitroxides", *Journal of Magnetic Resonance,* 9:513–516 (1973).

Janzen, et al., "New 2–Substituted Pyrroline–N–oxides: An EPR Solvent Study of the Radical Spin Adducts", *Magnetic Resonance Chem.,* 32:711–720 (1994).

Janzen & Zhang, "Identification of Reactive Free Radicals with a New $^{31}$P–Labeled DMPO Spin Trap", *J. Org. Chem.,* 60:5441–5445 (1995).

Janzen, et al., "Synthesis and Spin–Trapping Chemistry of 5,5–Dimethyl–2–(trifluoromethyl)–1–pyrroline N–Oxide", *J. Org. Chem.,* 60:5434–5440 (1995).

Janzen, et al., "Mass Spectroscopy and Chromatography of the Trichloromethyl Radical Adduct of Phenyl Tert–Butyl Nitrone," *Free Rad. Res. Comms.,* 9(3–6)353–360 (1990).

Janzen, et al., "The Effect of Phenyl Tert–butyl Nitrone (PBN) on $CCI^4$–Induced Rat Liver Injury Detected by Proton Magnetic Resonance Imaging (MRI) In Vivo and Electron Microscopy" *Free Rad. Res. Comms.,* 9(3–6):325–335 (1990).

Janzen & Zhang, EPR Spin Trapping Alkoxyl Radicals with 2–Substituted 5,5–Dimethylpyrroline–N–oxides (2–XM2PO's)*, *J. Mag. Res.,* 101B:91–93 (1993).

Janzen & Evans, "Rate Constants for the Addition of Phenyl Radicals to N–(tert–Butyl)–α–phenylnitrone (Spin Trapping) and Benzene (Phenylation) as Studied by Electron Spin Resonance", *J. Am. Chem. Soc.,* 97(1):205–206 (1975).

Janzen, et al., "Synthesis of a Novel Nitrone, 2–Phenyl–5, 5–Dimethyl–1–Pyrroline N–Oxide (nitronyl–$^{13}$C), for Enhanced Radical Addend Recognition and Spin Adduct Persistence", *J. Am. Chem. Soc.,* 116(9): 3738–3743 (1994).

Janzen, et al., "On Spin Trapping Hydroxyl and Hydroperoxyl Radicals", *Canadian Journal Chemistry,* 56(17)2237–2242 (1978).

Janzen & Haire, in "Advances in Free Radical Chemistry", D.D. Tanner, Ed., JAI Press, Greenwich, CT, vol. 1, Ch. 6, 253–295 (1990).

Janzen, et al., "Spin Trapping Chemistry of 3,3,5,5–tetramethylpyrroline–N–oxide: an Improved Cyclic Spin Trap", *Can. J. Chem.,* 59(4):756–758 (1981).

Janzen, et al., "Proposed Mechanism for Production of Stable Aminoxyl Radical Impurities in the Synthesis of Substituted 5,5–Dimethylpyrroline–N–oxide (DMPO) spin Traps", *Chemistry Letters,* No. 3:497–500 (1993).

Janzen, et al., "Substituent Effect on the Stability of the Hydroxyl Radical Adduct of α–Phenyl N–tert–Butyl Nitrone (PBN)", *Tetrahedron Lett.,* 33:1257–1260 (1992).

Janzen, et al., "Stabilities of Hydroxyl Radical Spin Adducts of PBN–Type Spin Traps", *Free Rad. Biol. and Medicine,* 12(2):169–173 (1992).

Janzen, et al., An ENDOR Study of Radical Spin Adducts Derived from Novel 2–Substituted–5,5–Dimethyl–Pyrroline–N–Oxide Spin Traps, *Appl. Magn. Reson.,* 6:511–519 (1994).

Janzen, et al., "Biological Spin Trapping II. Toxicity of Nitrone Spin Traps: Dose–Ranging in the Rat", *J. Biochemical and Biophysical Methods,* 30:239–247 (1995).

Kauffman, Jr. & Grossman, "Prostaglandin and Cimetidine Inhibit the Formation of Ulcers Produced by Parenteral Salicylates," *Gastroenterology,* 75(6):1099–1102 (1978).

Keana, et al., "Azethoxyl Nitroxide Spin–Labeled Crown Ethers and Cryptands with the N–O Group Positioned Near the Cavity", *J. Org. Chem.,* 48:2467–2654 (1983).

Keana, et al., "Difunctionalized Trans–2,5–Disubstituted Pyrrolidine (Azethoxyl) Nitroxide Spin–Labels", *J. Org. Chem.,* 48:2644–2647 (1983).

Kindy, et al., "Ischemic Induction of Protooncogene Expression in Gerbil Brain", *J. Mol Neurosci.,* 2:217–228 (1991).

Kotake & Janzen, "Decay and Fate of the Hydroxyl Radical Adduct of α–Phenyl–N–tert–butylnitrone in Aqueous Media", *J. Am. Chem. Soc.,* 113:9503–9506 (1991).

Kotake, et al., "Determination of the Rate of Superoxide Generation from Biological Systems by Spin Trapping: Use of Rapied Oxygen Depletion to Measure the Decay Rate of Spin Adducts", *Free Rad. Biol. and Medicine,* 17:215–223 (1994).

Lai, et al., "In vivo Spin Trapping of Free Radicals Generated in Brain, Spleen, and Liver during Gamma Radiation of Mice," *Arch. Biochem. Biophys.,* 244:156–160 (1986).

Lee & Keana, "Nitroxides Derived from 3,4–Dihydro–2, 5–Dimethyl–2H–pyrrole 1–Oxide: A New Series fo Minimum Steric Perturbation Lipid Spin Labels", *J. Org. Chem.,* 43(21):4226–4231 (1978).

Makino, et al., "Chemical Effects of Ultrasound on Aqueous Solutions. Evidence for OH and H by Spin Trapping", *Journal American Chemistry Society,* 104:3537–3539 (1982).

Masini, et al., "Ischemia–Reperfusion Injury and Histamine Release in Isolated Guinea–Pig Heart: The Role of Free Radicals", *Agents and Actions,* 27(1/2):154–157 (1989).

McCord, "Oxygen–Derived Free Radicals in Postischemic Tissue Injury", *New England J. of Med.,* 312(3):159–163 (1985).

McKechnie, et al., "Modification by Oxygen Free Radical Scavengers of the Metabolic and Cardiovascular Effects of Endotoxin Infusion in Conscious Rats", *Circulatory Shock,* 19:429–439 (1986).

Mitsuta, et al., "A Kinetic Analysis of Superoxide Adduct Formation in the Presence of Typical Scavengers", *Bull. Chem. Soc. Jpn.,* 67:529 (1994).

Novelli, et al., "Phenyl–T–Butyl–Nitrone is Active Against Traumatic Shock in Rats," *Free Radic. Res. Commun.,* 1(5):321–327 (1986).

Novelli, et al., "Oxygen Free Radicals in Shock", Int. Workshop Florence 1985, 119–124 (Karger, Basel 1986).

Novelli, et al., Free Radicals in Liver Injury, 225–228 (IRL Press, Oxford, England, 1985).

Novelli, et al., "Spin–Trappers and Vitamin E Prolong Endurance to Muscle Fatigue in Mice," *Free Radical Biol. Med.,* 8:9–13 (1990).

Oehler & Janzen, "Simulation of Isotropic Electron Spin Resonance Spectra: A Transportable Basic Program", *Can. J. Chem.,* 60:1542–1548 (1982).

Oliver, et al., "Oxidative Damage to Brain Proteins, Loss of Glutamine Synthetase Activity, and Production of Free Radicals During Ischemia/Reperfusion–Induced Injury to Gerbil Brain", *Proc. Natl. Acad. Sci. USA,* 87:5144–5147 (1990).

Packer & Glazer, *Methods in Enzymology,* vol. 186, "Oxygen Radicals in Biological Systems, Part B, Oxygen Radicals and Antioxidants", San Diego, Academic Press (1990).

Perkins, "Spin Trapping", Department of Chemistry, Chelsea College, London, England.

Petkova, et al., "Noradrenaline and Adrenaline in the Adrenal Glands and Myocardium During Endotoxin Shock and Antioxidant Therapy", 12:223–227 (1986).

Petkova, et al., "Changes in the Glucocorticoids Secretion During Endotoxin Shock and Antioxidants Treatment", *Agressologie,* 28(8):833–834 (1987).

Piccinini, et al., "Pharmacological Action of a New Spin Trapping Compound, 2–Phenyl DMPO, in the Adriamycin–Induced Cardiotoxicity", *Free Rad. Res.,* 23(1):81–87 (1994).

Phillis & Clough–Helfman, "Protection from cerebral ischemic injury in gerbils with the spin trap agent N–tert–butyl–α–phenylnitrone (PBN)," *Neurosci. Letters,* 116:315–319 (1990).

Plummer, et al., "Free Radical Foundation in Vivo and Hepatotoicity Due to Anesthesia with Halothane", Anesthesiology, 57:160–166 (1982).

Rainsford, K.D., "Prostaglandins and the Development of Gastric Mucosal Damage by Anti–Inflammatory Drugs," *Agents Action,* 6(Suppl):193–212 (1979).

Rainsford, K.D., "Electronmicroscopic Observations On the Effects of Orally Administered Aspirin and Aspirin–Bicarbonate Mixtures On the Development of Gastric Mucosal Damage in the Rat," *Gut,* 16:514–527 (1975).

Rainsford, "Gastrointestinal Damage from Nonsteroidal Anti–Inflammatory Drugs," *Toxicologic Pathology,* 16(2):251–259 (1988).

Rau, et al., "Direct Observation of Spin–Trapped Carbon Dioxide Radicals in Hepatocytes Exposed to Carbon Tetrachloride," *Free Rad. Res. Comms.,* 9(3–6):197–204 (1990).

Reinke, et al., "Possible Roles of Free Radicals in Alcoholic Tissue Damage," *Free Rad. Res. Comms.,* 9(3–6):205–211 (1990).

Reznikov, et al., "Recyclization of Imidazoline Enaminoketones: A New Route to Nitroxide Derivatives of Bicyclo[3, 2,1] Azooctane" *Abstracts: International Conference on Nitroxide Radicals* (1989).

Rosen & Turner, "Synthesis of Spin Traps Specific for Hydroxyl Radical," *J. Med. Chem.,* 31:428–432 (1988).

Royston, "Free Radicals", *Anaesthesia,* 43:315–320 (1988).

Schaefer, et al., "Blood Chemistry Changes in the Rat Induced by High doses of Nitronyl Free Radical Spin Traps", *Free Radical Biol. Med.,* 21(4):427–36 (1996).

Sentjurc, et al., "Metabolism, Toxicity, and Distribution of Spin Traps", Chapter 10, 199–206, *Biological Applications of Electron Spin Resonance* (NY: Wiley & sons, 1992).

Siesjo, "Mechanisms of Ischemic Brain Damage", *Critical Care Medicine,* 16(10):954–963 (1988).

Smith, et al., "Gastric Mucosal Injury in the Rat. Role of Iron and Xanthine Oxidase," *Gastroenterol.,* 92:950–956 (1987).

Sridhar, et al., "Spin Trapping Agents Protect Against Microsomal Lipid Peroxidation," *Oxygen Radicals Chem. Biol.,* pp. 309–315, Proc. 3d Int. Conf. Jul. 10–15, 1983 (publ. 1984) (abstract).

Swartz, et al., "Summary and Conclusions", Chapter 11, 207–209, *Biological Applications of Electron Spin Resonance* (NY: Wiley & sons, 1992).

Tomasi & Iannone, "ESR Spin–Trapping Artifacts in Biological Model Systems", Chapter 9, *Biological Magnetic Resonance,* 13:353–384 (1993).

Towner, et al., "Enhancement of Carbon Tetrachloride–Induced Liver Injury by a Single Dose of Ethanol: Proton Magnetic Resonance Imaging (MRI) Studies In Vivo," *Biochim. Biophysica Acta,* 1096(3):222–230.

Towner, et al., "MRI Study of the Inhibitory Effect of New Spin Traps on in Vivo CCI4–Induced Hepatotoxicity in Rats", *Free Radical Biology & Med.,* 14:677–681 (1993).

Tuccio, et al., "Decay of the Hydroperoxyl Spin Adduct of 5–Diethoxyphosphoryl–5–methyl–1–pyrroline N–Oxide: An EPR Kinetic Study", *J. Chem. Soc., Perkin Trans.,* 2:295–298 (1995).

Turner & Rosen, "Spin Trapping of Superoxide and Hydroxyl Radicals with Substituted Pyrroline 1–Oxides", *J. Med. Chem.,* 29:2439–2443 (1986).

Weglickl, et al., Oxy Radicals in Molecular Biology and Pathology, 357–364 (Proceedings of an Upjohn–UCLA Symposium held at Park City, Utah, (Jan. 24–30, 1988) Editor: Alan R. Liss, Inc. NY (abstract).

Whittle & Vane, "A Biochemical Basis for the Gastrointestinal Toxicity of Non–steroid Antirheumatoid Drugs," *Arch. Toxicol.,* 7(Suppl.):315–322 (1984).

Yamazaki, et al., "Kinetic Studies on Spin Trapping of Superoxide and Hydroxyl Radicals Generated in NADPH–Cytochrome P–450 Reductase–Paraquat Systems", *J. Biol. Chem.,* 265:652–659 (1990).

Yanev, et al., Oxygen Free Radicals in Shock, Int. Workshop, Florence 1985, 193–196 (Karger, Basel 1986) (abstract).

Yu, et al., "Synthesis of 4–Azahomoadamant–4–Ene N–Oxides and Their 1,3–Dipolar Cycoaddition Reactivity[1]", *Tetrahedron Letters,* 32(37):4965–4968 (1991).

Zhang, et al., "Synthesis and Plande Selective Spin Trapping of a Novel Trap 5,5–Dimethyl–3(2–ethoxycarbonylethyl)–1–pyrroline N–oxide", *Z. Naturforsch.,* 45b:1075–1083 (1990).

Zhang & Xu, "ESR Evidence for the Stereospecific Spin Trapping of 5–Alkyl–5–Methyl–1–Pyrroline N–oxides", *Mag. Res. Chem.,* 27:846–851 (1989).

Zang & Janzen, "An EPR and MS Investigation of Hexa––Substituted Pyrrolidine–1–oxyl Aminoxyl Stable Radicals. Unexpectedly Large y–Hydrogen Splittings" *Z. Naturforsch.,* 50b:1–6 (1995).

Tufariello et al, 1978, Tetrahedron Letters, No. 20, pp. 1733–1736 A Sterospecific Synthesis of (±) Cocaine.

North et al, 1992, J. Biol. Chem., vol. 267, No. 9, pp. 5743–5746, "Detection of Lipid Radicals by Electron Paramagnetic Resonance Spin Trapping".

Cheng et al, 1993, Free Radical Biology & Medicine, vol. 14, pp. 243–250 "Distribution of Spin Trapping Compounds in Rat Blood and Brain: In vivo Microdialysis Determination".

Zajac et al (1988), J. Org. Chem, vol. 53, No. 25, pp. 5856–5860, "Oxidation of Amines with 2–Sulfonyloxaziridines (Davis' Reagents)".

Becker, 1996, J. Am. Chem. Soc. vol. 118, No. 4, pp. 905–906, Highly Sensitive Colorimetric Detection and Facile Isolation of Diamagnetic Free Radical Adducts of Novel Chromotropic Nitrone Spin Trapping Agents Readily Derived from Guaiazulene.

Tufariello et al, 1979, J. Am. Chem. Soc., vol. 101, No. 9, pp. 2435–2442, Synthesis in the tropone class of alkaloids. Pseudotropine and dl–Cocaine.

Sankuratri et al, 1996, Tetrahedron Letters, vol. 37, No. 30, pp. 5313–5316, "Synthesis and Spin Trapping Chemistry of a Novel Bicyclic Nitrone: 1,3,3–Trimethyl–6–azabicyclo [3.2.1]oct–6–ene N–oxide (Trazon)".

Jurkiewicz et al, 1996, Photochemistry and Photobiology, vol. 64, No. 6, pp. 918–922, "EPR Detection of Free Radicals in UV Irradiated Skin: Mouse versus human".

Mullen, 1978, Dissertation Abstracts International B, vol. 39, No. 1, p. 237–B "An approach to the Spiro System of Cephalotaxine and the total synthesis of (±) cocaine using nitrones".

Tegeler, 1977, Dissertation Abstracts International B, vol. 38, No. 3, p. 1220B, "A Nitrone Approach to the lupin alkaloids and Cocaine".

TABLE 2: TRAZON SPIN ADDUCTS

| TRAZON ADDUCT | SOLVENT | REAGENT/ METHOD | HYPERFINE SPLITTING CONSTANTS, G | | | | | |
|---|---|---|---|---|---|---|---|---|
| | | | N | $\beta H_1$ | $\beta H_2$ | $\gamma H_1$ | $\gamma H_2$ |
| Trazon-OH | Water | 1% $H_2O_2$/hv | 15.0 | 9.7 | 9.7 | 1.1 | 1.0 |
| Trazon-OH | Benzene | 1% $H_2O_2$/hv | 12.8 | 9.2 | 8.4 | 1.2 | 1.2 |
| Trazon-nBuO | Benzene | nBuONO/hv | 13.2 | 8.8 | 6.4 | 1.3 | 1.1 |
| Trazon-tBuO | Benzene | tBuOOH/hv | 13.1 | 8.8 | 8.0 | 1.2 | 1.2 |
| Trazon-OOH | Water | Riboflavin/hv | 14.5 | 9.7 | 8.3 | 1.3 | 1.1 |
| Trazon-Me | Benzene | MeMgBr | 14.2 | 13.8 | 8.5 | 1.2 | 1.2 |
| Trazon-Ethyl | Benzene | EtMgBr | 14.2 | 13.6 | 8.6 | 1.1 | 2(1.2) |
| Trazon-Phenyl | Benzene | PAT/80°C | 14.9 | 14.05 | 8.5 | 1.4 | 1.4 |
| Trazon-OC(CH$_3$)$_2$CN | Benzene | AIBN/80°C | 13.0 | 8.8 | 7.9 | 1.1 | 1.1 |
| Trazon-OMe | MeOH | MeOH/hv | 13.2 | 9.0 | 8.5 | 1.2 | 1.2 |
| Trazon-CH(CH$_3$)OH | EtOH | EtOH/hv | 15.4 | 14.8 | 9.25 | 1.45 | 1.45 |
| Trazon-C(CH$_3$)$_2$OH | isoPropanol | iPrOH/hv | 14.8 | 17.7 | 8.8 | 1.4 | 1.2 |

FIGURE 3

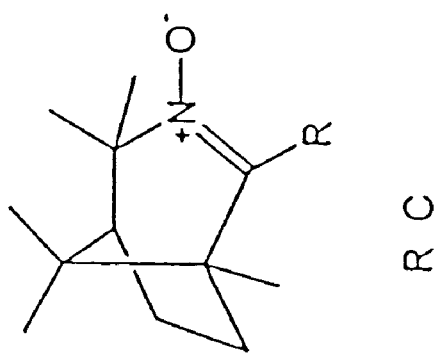
R C
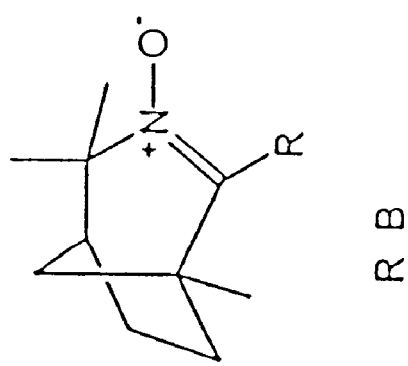
R B
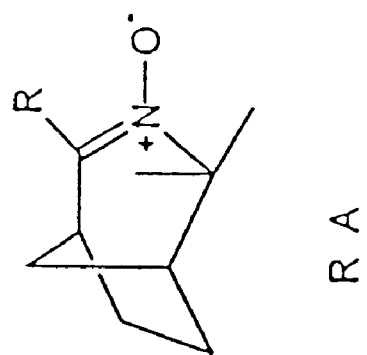
R A
FIGURE 4

MULTICYCLIC NITRONE SPIN TRAPPING COMPOSITIONS

The government may have certain rights in this invention pursuant to NIH Grant RR05517.

BACKGROUND OF THE INVENTION

The present invention is generally in the area of bicyclic nitrone spin trapping compositions which are capable of reacting with free radicals to produce a detectable radical spin adduct.

The superoxide radical anion and the hydroxyl radical both play significant roles in the events of free radical injury to biological systems under oxidative stress. Research in recent years indicates that in most cases of oxidative damage, superoxide is the species that initiates free radical reactions that follow. Superoxide often is the precursor to the generation of the hydroxyl radical, which is considered to be most reactive oxygen-centered radical known. Therefore, detection and quantitation of superoxide anion and hydroxyl radicals in biological systems is very important in order to verify that the observed events are indeed caused by free radicals as well as to elucidate the relationship between the amount of free radical generated and its outcome. Halliwell and Gutteridge, *Free Radicals in Biology and Medicine*, Second Edition, Oxford, Clarendon Press, 1989; Packer and Glazer, *Methods in Enzymology*, Vol. 186, *Oxygen Radicals in Biological Systems, Part B, Oxygen Radicals and Antioxidants*, San Diego, Academic Press, 1990. Because oxygen radicals are labile in nature there is no perfect method available for their detection and quantitation.

Nitrones have been developed as useful spin traps for the detection of free radicals. The spin trapping chemistry of nitrones has been extensively reviewed, for example in: Janzen, E. G., *Accounts of Chemical Research*, 4, 31–40 (1971); Janzen, E. G. and Haire, D. L., *Advances in Free Radical Chemistry*, edited by D. D. Tanner, JAI Press Inc., Greenwich, Conn., USA Ch. 8, pp. 253–295 (1990); Perkins, M. J., *Chemical Society Special Publication #24*, Ch. 5, (1970); and Perkins, M. J., "Spin Trapping", in *Advances in Physical Organic Chemistry*, Edited by V. Gold and D. Bethell, Academic Press, New York, N.Y. Vol. 17, pp. 1–58, (1980). In general, the known reactions indicate that free radicals add to the carbon atom to produce nitroxides, and not to the oxygen atom or the nitrogen atom of the nitrone function. The nitroxides so produced have variable stability and this intrinsic stability depends on the polarity of the solvent. Kotake, Y. and Janzen, E. G., *J. Am. Chem. Soc.*, 113, 9503–9506 (1991); Janzen, E. G. et al., *Free Radical Biology and Medicine*, 12, 169–173 (1992); and Janzen, E. G. et al., *Tet. Lett.*, 33, (10) 1257–1260 (1992). Nitroxides also can be reduced or oxidized in the presence of extrinsic factors such as disproportionation reactions, redox reagents which either oxidize or reduce the nitroxide spin adduct, or subsequent additional spin trapping reactions. Janzen, E. G. et al., *J. Am. Chem. Soc.*, 112, 8279–8284 (1990).

DMPO (5,5-dimethylpyrroline-N-oxide) has become the most commonly used spin trap in biological systems. The use of 5,5-dimethylpyrroline-N-oxide (DMPO) as a versatile spin trap was first published in: E. G. Janzen and J. I.-P. Liu, *J. Mag. Res.*, 9:510–512 (1973). DMPO is useful to detect radicals because the hydroxyl radical spin adduct and the superoxide/hydroperoxyl radical spin adduct have distinctive EPR spectra. Janzen and Liu, *Journal Magnetic Resonance*, 9:510 (1973); Janzen et al., *Canadian Journal Chemistry*, 56:2237 (1978); Finkelstein et al., *Journal American Chemistry Society*, 102:4994 (1980); and Makino et al., *Journal American Chemistry Society*, 104:3537 (1982). These unique signatures are readily recognized in the presence of each other and thus are convenient for the study of systems where both the hydroxyl and superoxide/hydroperoxyl radicals are produced simultaneously. Moreover, since EPR spectroscopy is very sensitive, the spin trapping method permits the detection of low concentrations of these two species in in situ experiments.

The life-times for some DMPO spin adducts sometimes are low, depending on the structure of the radical. For example, the half-life of the superoxide adduct in neutral media is only about one minute. Finkelstein et al., *Mol. Pharmacol.*, 16:676 (1979); Finkelstein et al., *Arch. Biochem. and Biophys.*, 200:1 (1980); Janzen and Haire, in *Advances in Free Radical Chemistry*, D. D. Tanner, Ed., JAI Press, Greenwich, Conn., vol 1, pp 253–295 (1990); Buettner and Oberly, *Biochem. Biophys. Res. Com.*, 83:69 (1978); Yamazaki et al., *J. Biol. Chem.*, 265:652 (1990); Buettner, *Free Rad. Res. Commun.*, 19, (S1), S228–S230 (1993); and Mitsuta et al., *Bull. Chem. Soc. Jpn.*, 67:529 (1994). Therefore the intensity of the EPR signal is not proportional to the superoxide generated in the system. Also, in biological systems DMPO seems to almost exclusively concentrate in polar regions since this nitrone is very water soluble and the partition coefficient for lipid phases is very small (0.1:1). Turner and Rosen, *J. Med. Chem.* 29:2439–2444 (1986).

Derivatives of DMPO also have been prepared and their spin trapping chemistry explored, however the derivatives have serious drawbacks ranging from complex EPR spectra of spin adducts, to expensive necessary pathways for synthesis. Janzen et al., *Can. J. Chem.*, 59:756–758 (1981); Rosen and Turner, *J. Med. Chem.*, 31:428–432 (1988); Haire and Janzen, *Can. J. Chem.*, 60:1514–1522 (1982); Janzen et al., *J. Mag. Res.*, 9:513–516 (1973); Janzen and Zhang, *J. Mag. Res.*, 101B:91–93 (1993); Janzen et al.,*J. Org. Chem.*, 60:5434–5440 (1995); Barasch et al., *J. Am. Chem. Soc.*, 116:7319–7324 (1994); Janzen et al., *J. Am. Chem. Soc.*, 116: 3738–3743 (1994) and Janzen et al., *Chemistry Letters*, 497–500 (1993); Frejaville et al., *J. Chem. Soc., Chem. Commun.*, 1793–1794 (1994); and Tuccio et al., *J. Chem. Soc., Perkin Trans.*, 2:295 (1995).

The biological applications of nitrone spin traps have been reviewed, for example in: Janzen, E. G., *Free Radicals in Biology*, 4, 115 (1980); and Janzen, E. G., "Spin Trapping", in "Oxygen Radicals in Biological Systems", *Methods in Enzymology*, L. Packer, editor, Academic Press, Inc., New York, N.Y., 105, 188–198 (1984); DeGray, J. A. and Mason, R. P. "Biological Spin Trapping" in *Electron Spin Resonance*, Vol. 14, "The Royal Society of Chemistry, A Specialist Periodical Report, A Review of Recent Literature to 1993" Ch. 8. pp. 246–319; Tomasi, A. and Iannone, A. "ESR Spin-Trapping Artifacts in Biological Model Systems" in Biological Magnetic Resonance, Vol. 13, EMR of Paramagnetic Molecules, edited by L. J. Berliner and J. Reuben, Plenum Press, New York, N.Y. ch. 9. pp. 353–384 (1993); and Sentjurc, M. et al., "Metabolism, Toxicity and Distribution of Spin Traps", in *Nitroxide Spin Labels; Reactions in Biology and Chemistry*,CRC Press, New York, N.Y. Ch. 10. pp. 199–209 (1995). These reviews mainly describe examples of the use of nitrones to detect free radicals in vitro or in vivo.

In general, nitrones with aliphatic or aryl groups attached to the nitrone function are the most useful for spin trapping. Janzen, E. G. and Haire, D. L. *Advances in Free Radical Chemistry*, edited by D. D. Tanner, JAI Press Inc., Greenwich, Conn., USA Ch. 8, pp. 253–295 (1990). Alicyclic nitrones have been described with the nitronyl function incorporated into the cyclic structure. Janzen, E. G. and Liu, J. I-P. *J. Mag. Res.*, 9, 510–512 (1973); Janzen, E. G. et al., *Can. J. Chem.*, 59, 756–758 (1981); and Zhang, Y.-K. and Janzen, E. G., Z. *Naturforsch.* (B), 50, (10), 1531– 1536 (1995). The toxicity of nitrone compounds also has been examined. Janzen, E. G. et al., *J. Biochem. Biophys. Methods*, 30, 239–247 (1995).

The synthesis of tricyclic 4-azahomoadamant-4-ene N-oxides and their 1,3-dipolar cycloaddition reactions with alkynes have been reported. Yu et al., *Tetrahedron Letters*, 32:4965–4968 (1991). The synthesis of nitroxide derivatives of bicyclo[3,2,1]-azooctane also has been described. Reznikov et al., *International Conference on Nitroxide Radicals*, Abstract, Sep. 18–23, 1989. The use of bicyclic nitrones as spin trapping compositions has not been explored.

There is a need for the development of spin trapping compounds for detecting free radicals in biological systems. There is a need for the development of methods for synthesizing spin trapping compounds capable of forming spin adducts with longer half-lives for use in biological systems. There also is a need for the development of methods for the synthesis of spin trapping compounds with low toxicity for animals when used in vivo. There further is a need for the development of spin trapping compounds which are capable of forming spin adducts with radicals which are readily identifiable spectrophotometrically.

It is therefore an object of the invention to provide methods for synthesizing spin trapping compounds capable of reacting with free radicals in biological systems. It is another object of the invention to provide spin trapping compounds which are capable of forming stable spin adducts with characteristic and readily identifiable electron paramagnetic resonance ("EPR") spectra. It is yet another object of the invention to provide spin trapping compounds which can be used in diagnostic and therapeutic applications.

SUMMARY OF THE INVENTION

Multicyclic nitrone spin trapping compounds capable of forming stable free radical adducts are provided, as well as methods for their synthesis. The multicyclic nitrone spin trapping compounds may be reacted with any of a wide range of different free radicals, such as hydroxyl or hydroperoxyl radicals, in solution, to form stable spin adducts which are readily detectable by electron paramagnetic resonance ("EPR") spectroscopy. The multicyclic nitrone spin trapping compounds may be used to detect free radicals in a sample such as a biological fluid sample. In one embodiment, the spin trapping compound, 1,3,3-trimethyl-6-azabicyclo-[3.2.1]oct-6-ene-N-oxide ("TRAZON") is provided, as well as methods for the synthesis of TRAZON and of modified forms of TRAZON. TRAZON can react with a wide range of different free radicals in solution to form free radical spin adducts which are readily detectable by EPR.

BRIEF DESCRIPTION OF THE DRAWINGS

FIG. 3 is a list of spin adducts of 1,3,3-trimethyl-6-azabicyclo[3.2.1]oct-6-ene-N-oxide ("TRAZON") formed from reaction of TRAZON with the corresponding free radical, and the hyperfine splitting constants of each adduct obtained by electron paramagnetic resonance ("EPR") spectroscopy.

FIG. 4 shows compounds formed by reaction of TRAZON, and the spin trapping compounds, A, B, and C with a Grignard or organolithium reagent.

DETAILED DESCRIPTION OF THE INVENTION

Multicyclic nitrone spin trapping compounds and methods for their synthesis are provided. Multicyclic compounds including at least two rings, such as bicyclic or tricyclic compounds, which include a nitrone functionality are provided which can react with radicals, such as hydroxyl or superoxide radicals, to form detectable spin-adducts. The multicyclic nitrone spin trapping compounds may be reacted with radicals in biological systems to form free radical spin adducts which may be readily identified spectroscopically. The multicyclic nitrone compounds are derived from naturally occurring or synthetic multicyclic compounds using synthetic organic reactions available in the art. Multicyclic nitrone spin trapping compounds can be synthesized and selected which can form detectable, stable spin adducts, have low toxicity, and have desired solubility properties.

Multicyclic Nitrone Spin Trapping Compounds

Multicyclic nitrone spin trapping compounds having two or more rings within the structure of the compound may be synthesized using organic chemistry techniques available in the art. The multicyclic nitrone spin trapping compounds may be derived from compounds which are preferably multicyclic, and which are natural products isolated from organisms such as plants, or which are synthetic compounds available in the art. The multicyclic compounds preferably have the nitronyl function incorporated into at least one ring in the compound. In a preferred embodiment, bicyclic compounds, such as TRAZON, are provided, wherein the nitronyl function is incorporated within two rings in the compound structure.

i. Bicyclic Nitrones

The bicyclic nitrone spin trapping compound in one embodiment is defined by Formula 1:

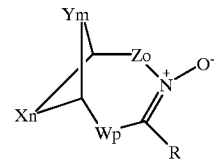

wherein
Xn is $(CH_2)n$ where n=1, 2 or 3; O; or N;
Ym is $(CH_2)m$ where m is 1, 2 or 3; O; or N;
Zo is $(CH_2)o$ where o is 0, 1, 2 or 3; or $C(CH_3)_2$;
Wp is $(CH_2)p$ where p is 0, 1, 2 or 3; and
R is H; $C_1$–$C_{12}$ alkyl; aryl, for example phenyl; or pyrridine-N-oxide.

ii. Formation of Multicyclic Nitrones

In one embodiment, the multicyclic nitrone spin trapping compounds are derived from naturally occurring multicyclic compounds, such as non-toxic natural products isolated from organisms such as plants. The nitrone compounds can be derived from a wide range of natural products available in the art which have certain known physiological effects such as taste, fragrance, narcosis, therapeutic effects such as pain relief, and flavor.

Figure 1:
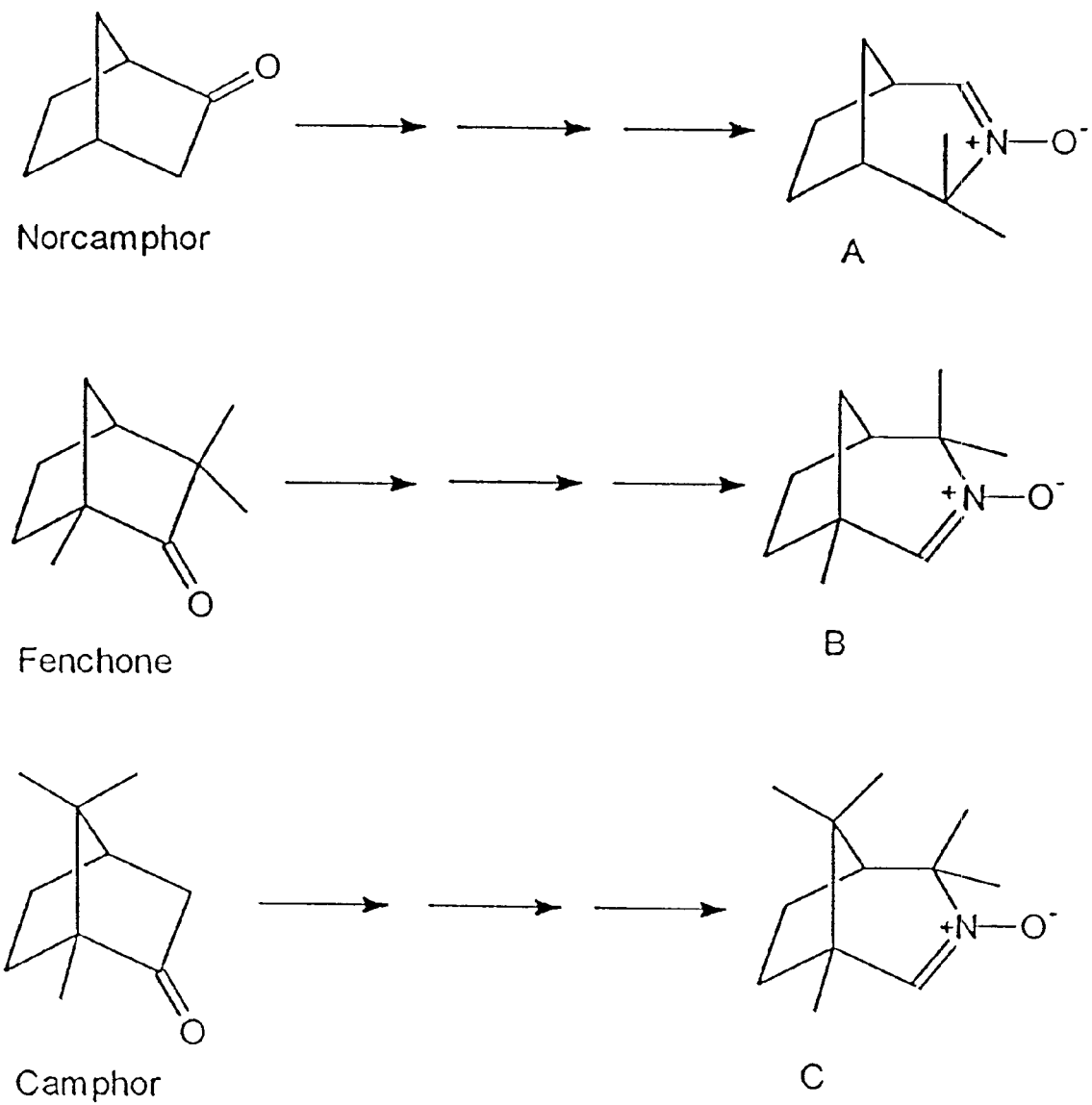
FIG. 1 shows schematically the derivation of the bicyclic nitrone spin trapping compounds, A, B and C from the natural products, norcamphor, fenchone, and camphor.
Figure 2:
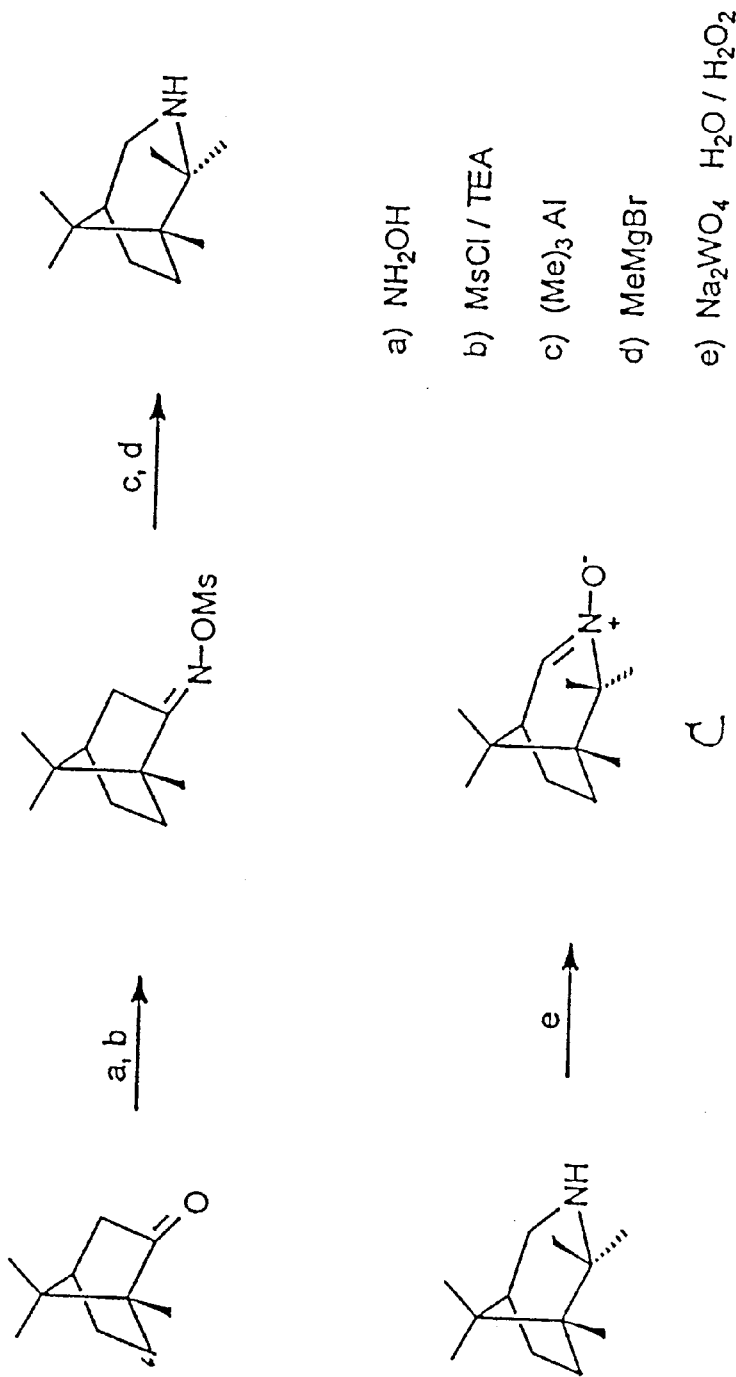
FIG. 2 shows schematically the synthesis of the bicyclic nitrone spin trapping compound, C, from camphor.

Multicyclic nitrones may be synthesized from natural products using synthetic organic reactions available in the art. As illustrated schematically in FIG. 1, in one embodiment, the bicyclic nitrone spin trapping compounds, A, B and C may be synthesized using synthetic organic reactions and reagents available in the art, from the natural products norcamphor, fenchone and camphor, respectively. A detailed pathway as an example for the synthesis of the bicyclic nitrone spin trapping compound, C, from camphor using synthetic organic chemistry reactions and reagents is shown in FIG. 2.

Generally, the nitrone compounds can be derived from natural products or synthetic compounds utilizing synthetic organic reactions available in the art. Other exemplary compounds from which the multicyclic nitrone spin trapping compounds may be derived include: adamantane; aldrin; anisotropine methylbromide; aphylline; apoquinine; apoatropine; atropine; atropine N-oxide; morphine analgetics such as 1,7-benzomorphan; benzoylecgonine; benzylmorphine; strychnine and naturally occurring and synthetic derivatives such as brucine; butropium bromide; n-butyl scopolammonium bromide; benztropine mesylate; bornyl chloride; camphor and substituted camphor molecules such as exobromocamphor and endobromocamphor; cafestol; camphene; d-camphocarboxylic acid; camphorsulfonic acid; chlorbicyclen; n-(3-chloroallyl)hexaminium choride; cinchonamine; camphotamide; chlordane; carbic anhydride; chlordecone; chrysanthenone; cinchonidine; cinnamoylcocaine; cocaine; cupreine; cyclothiazide; dieldrin; ecgonidine; ecgonine; clidinium bromide; diacetyldihydromorphine; codeine; cyprenorphine; deptropine; desomorphine; dihydromorphine; cyclorphan; cyoctal; endrin; euprocin; fenchone; glibornuride; hydroquinidine; hydroquinine; epiquinidine; epiquinine; fencamfamine; homotropine; hydroxycamphor; eucalyptol; ipratropium bromide; fentonium bromide; hydrocodone; hydromorphine; hydroxycodeinone; metapon; hyoscyamine; oxitropium bromide; isoborneol; isobenzan; methscopolamine; myrtecaine; myxin; pseudopelletierine; lycopodine; morphine; mycophine; norea; olaquindox; pseudotropine; mecamylamine; mirex; phenazocine; normorphine; quinine; β-santalol; tropine and esters thereof such as tropine benzylate; tropacine; tropenzile; and tropacocaine.

The multicyclic nitrone spin trapping compound may be derived in one embodiment from multicyclic parent compounds which are natural products with characteristic known properties including flavors, such as fenchone, pain relievers, such as morphine and cocaine, topical chemicals for alleviating skin irritation, such as camphor, medicines such as quinine, and pesticides, such as chlordane.

In one preferred embodiment, the nitrone compound is derived from a bicyclic molecule which is a natural product or a synthetic compound, wherein the nitronyl function is incorporated into one of the ring structures. For example, the nitrone compound may be derived from bicyclic compounds such as camphor, morphine, norbornene, tropine, cinchonine, strychnine, quinine, pinene, myrtanol, adamantane, longifolene, isopinocamphenol, gibberelic acid, fenchone, isoborneol and brucine. In some embodiments, the structure of the multicyclic compound from which the nitrone is derived ("the parent compound") may be selected which has specific receptor binding properties which elicit a particular pharmacological effect. The structure of the parent compound thus may influence the binding and pharmacological effect of the multicyclic nitrone compound.

iii. The Synthesis of TRAZON

In one embodiment, the bicyclic nitrone, 1,3,3-trimethyl-6-azabicyclo[3.2.1]oct-6-ene-N-oxide, given the trivial name "TRAZON", is provided. TRAZON may be synthesized by oxidation of the commercially available secondary amine, 1,3,3-trimethyl-6-azabicyclo[3.2.1]octane, as described in detail in Example 1, and as shown below:

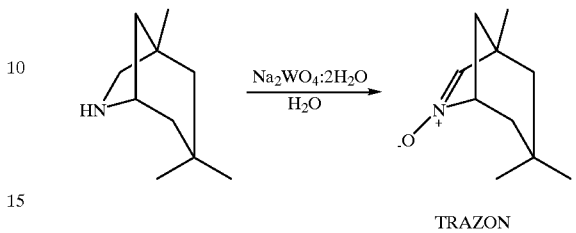

TRAZON

The electron paramagnetic resonance ("EPR") spectrum of a solution of TRAZON showed that the bicyclic nitrone was obtained in very pure form with a very clean baseline trace, and no detectable trace paramagnetic free radical impurities. Thus, TRAZON can be obtained in improved purity in comparison to many free radical trapping reagents such as DMPO. TRAZON is a stable, crystalline solid with a shelf life on the order of at least 6 months to 12 months or more. TRAZON advantageously reacts with a variety of radicals, including hydroxyl, t-butoxyl, hydroperoxyl, methyl, ethyl and phenyl radicals to produce a spin adduct with a distinct and clean EPR spectrum, which is different and characteristic for each radical trapped, as described in detail in Example 2.

iv. Modified Nitrones

The multicyclic nitrones, such as TRAZON, also can be modified using synthetic organic reactions available in the art. For example, Grignard reagents (RMgX) or organolithium compounds (RLi) can be added to nitrones using synthetic methods available in the art. Janzen and Blackburn, *J. Am. Chem. Soc.*, 91:4481–4490 (1969), the disclosure of which is incorporated herein by reference. After protonation with dilute acid a hydroxylamine is formed which can be can be oxidized to form a new nitrone, as shown schematically below:

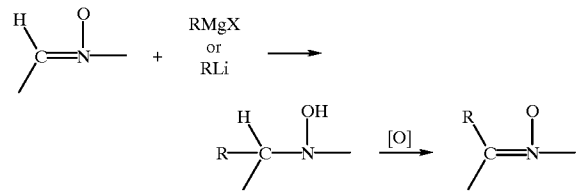

Other modified nitrones can be synthesized analogously using commercially available Grignard or organolithium reagents.

Examples of Grignard reagents available from commercial suppliers such as Aldrich Chemical Company, St. Louis, Mo., which can be used to form modified nitrones include RMgX, wherein X is halogen, typically Br, and wherein R is phenyl or aryl without nitro, cyano, or carbonyl groups, or R is branched or straight chain C1–C8 hydrocarbon. Examples of organolithium reagents which can be used include RLi, wherein R is: aryl, such as phenyl; alkyl, such as n-butyl; amidyl, such as 2-pyridyl; or phosphoranyl, such as diethylphosphoranyl.

Using these reagents, a variety of modified nitrones may be synthesized. For example, phenyl TRAZON, aryl TRAZONs, alkyl TRAZONs, 2-pyridyl TRAZONs, and diethylphosphoranyl TRAZONs may be synthesized. Thus, TRAZON, or the nitrones, A, B and C, may be reacted with a Grignard reagent, RMgX, or organolithium reagent, RLi, to form the compounds R-TRAZON, R—A, R—B, or R—C, shown in FIG. 4, where R is, for example, aryl, alkyl, amidyl, or phosphoranyl.

Free Radical Adducts

In one embodiment, the multicyclic nitrone compound can react with a free radical in a sample to produce a spin adduct of the multicyclic nitrone spin trapping compound and the free radical, and then the spin adduct can be detected, to determine the presence of the free radical in the sample. The free radical adducts can readily be detected by their characteristic electron paramagnetic resonance (EPR) spectrum. For example, a composition including the multicyclic nitrone spin trapping compound and a pharmaceutically acceptable carrier may be administered to a patient. The multicyclic nitrone spin trapping compound then is permitted to react with a free radical in the patient to produce a spin adduct of multicyclic nitrone spin trapping compound and the radical in the patient. The spin adduct then is detected, as an indicator of the presence of the radical in the patient.

Multicyclic nitrone spin trapping compounds can be synthesized and designed which form stable adducts with free radicals and can therefore be used to detect or trap free radicals in a sample, such as a biological system. The multicyclic nitrone spin trapping compounds can react with a variety of free radicals to form a spin adduct which may be detected spectrometrically, for example, by EPR. The compounds may form stable spin adducts, for example, with hydroxyl, hydroperoxyl, phenyl, aryl, trichloromethyl, alkyl, alkoxyl, acylalkoxyl, sulfur, nitrogen, halogen, hydrogen and phosphorous centered radicals.

In the multicyclic nitrones, a bridge structure may selected which reduces the intrinsic instability of the nitroxide spin adducts, for example due to β-bond cleavage. The stability of nitroxide spin adducts has been examined in Kotake and Janzen, *J. Am. Chem. Soc.* 113:9503–9506 (1991); Janzen et al., *Free Radical Biology and Medicine*, 12:169–173 (1992); and Janzen et al., *Tet. Lett.*, 33:1257–1260 (1992), the disclosures of which are incorporated herein by reference. Multicyclic nitrone spin trapping compounds can be selected which form, for example, stable hydroxyl and hydroperoxyl/superoxide radical spin adducts which have a sufficient half life and a characteristic EPR signal such that they can be readily detected by EPR. The multicyclic nitrone spin trapping compounds thus can be reacted with free radicals in a sample in either in vivo or in vitro diagnostic or therapeutic applications.

Therapeutic Applications

The multicyclic nitrone spin trapping compounds in association with a pharmaceutically acceptable carrier may be used in a variety of therapeutic applications. Disorders associated with the formation of free radicals may be treated by administering to a patient in need of treatment a composition including an effective amount of a multicyclic nitrone spin trapping compound in a pharmaceutically acceptable carrier, to reduce the quantity of the free radicals associated with the disorder. Multicyclic nitrones may be synthesized and selected for the treatment of diseases and disorders associated at least in part with the generation of free radicals as described, for example, in PCT WO 92/22290 published Dec. 23, 1992, and PCT WO 95/17876, published Jul. 6, 1995, the disclosures of which are incorporated herein by reference. For example, diseases or disorders of the central and peripheral nervous systems can be treated, as well as disorders arising from ischemia, infection, inflammation, ulcerative colitis, oxidation from exposure to radiation or cytotoxic compounds, as well as due to naturally occurring processes such as aging. Disorders of the central nervous system which can be treated include stroke, aging, Parkinsonism, concussion, aneurysm, ventricular hemorrhage and associated vasospasm, migraine and other vascular headaches, spinal cord trauma, and neuroanesthesia adjunct. Disorders of the peripheral nervous system which can be treated include diabetic peripheral neuropathy and traumatic nerve damage. Disorders of the circulatory and respiratory systems also can be treated.

Peripheral organ diseases associated with the formation of free radicals which also can be treated include atherosclerosis (both diabetic and spontaneous), chronic obstructive pulmonary disease (COPD), pancreatitis, pulmonary fibrosis due to chemotherapeutic agents, angioplasty, trauma, burns, ischemic bowel disease, wounds, ulcers and bed sores, lupus, ulcerative colitis, organ transplantation, renal hypertension, overexertion of skeletal muscle, and epistaxis (pulmonary bleeding). The spin trapping nitrones also may be used in treating a variety of dysfunctions or disorders characterized by oxidized proteins or lipids such as altered oxidation of low density lipoprotein, and dysfunction from exposure to radiation, including x-ray, ultraviolet, gamma and beta radiation, and cytotoxic compounds, including those used for chemotherapy for cancer and viral infections.

Multicyclic nitrone spin trapping compounds may be synthesized and selected which are capable of forming a stable complex with a free radical in vivo, such that as a result of this chemical bond formation, the free radical is no longer damaging to the cell. The multicyclic nitrones may be selected which are capable of trapping free radicals, such as hydroxy and superoxide radicals, while remaining non-toxic to normal cells. In those applications where the compound must reach the brain and other parts of the CNS, the compound must also be able to pass through the blood brain barrier. Multicyclic nitrone compounds may be selected and synthesized with the water and lipid solubility properties appropriate for different therapeutic applications.

The nitroxide spin adducts formed upon reaction of the multicyclic nitrone compounds with a free radical also may be combined with a pharmaceutically acceptable carrier, for use in a variety of therapeutic applications, for example, as superoxide dismutase mimics, as described in Veregin et al., *Macromolecules*, 28:4391–4398 (1995), antioxidants as described in Nilsson et al., *J. Biol. Chem.*, 264:1113 (1989), and "living polymer" chemical polymerizations, as described in Mitchell et al., *Biochemistry*, 29:2802–2807 (1990), the disclosures of which are incorporated herein by reference.

Derivatives and Conjugates

Multicyclic nitrone spin trapping compounds may be derivatized to alter certain functionality of the molecule, or may be conjugated to a second molecule using synthetic organic reactions available in the art. For example, multicyclic nitrone spin trapping compounds with improved lipophilicity, water solubility or stability can be designed and synthesized. In one embodiment, modified multicyclic nitrones can be synthesized, such as the modified TRAZON molecules described above, with α-substituent groups including alkyl, aryl, 2-pyridyl or diethylphosphoranyl.

The multicyclic nitrone spin trapping compounds also can be conjugated to other molecules such as a targeting molecule or a therapeutic molecule. For example, conjugates of calcium channel blockers such as nimodipine, nicardipine, nifedipine, nitrendipine, diltrazam, flunarazine, digitalis, propranalol, desferal, and lazaroids, antiinflammatories such as prednisone, antioxidants such as vitamin E, and neuroactive compounds such as L-DOPA and acetaminophen are possible, although in some cases spacers will be required between the spin-trapping compound and the conjugated compound in order to preserve maximum activity. Conjugates with targeting molecules such as antibodies or ligands for specific receptors (such as certain hormones, enzymes, or specific sugars or carbohydrates) can be used to target or otherwise concentrate the spin trapping compound. Additionally, a polymer of multiple units of the spin trapping compound can be formed.

Administration

The multicylic nitrone spin trapping compounds may be provided in a pharmaceutically acceptable carrier for a desired route of administration. The compounds can be administered in a suitable carrier, for example, parenterally, i.e., subcutaneously, intramuscularly, intracerebroventricularly, or intravenously and, alternatively, intrathecally. In appropriate carriers they also can be administered, for example, orally, topically or nasally.

Suitable pharmaceutical carriers are known to those skilled in the art. For example, when the active ingredient is administered parenterally, in sterile liquid dosage forms, the carrier can be water, a suitable oil, saline or other buffered physiological solution, aqueous dextrose or related sugar solutions and glycols, such as propylene glycol or polyethylene glycol. Exemplary pharmaceutical carriers are described in *Remington's Pharmaceutical Sciences*, 17th ed., Mack Publishing Co., Easton, Pa., p. 1418 (1985), a standard reference text in this field incorporated herein by reference). For topical application, the carrier can be an ointment or cream base, or a transdermal patch. Compositions for oral administration will generally include an inert diluent or an edible carrier. The compound can also be administered by controlled delivery devices, such as biodegradable polymers. Additionally, the compound may be administered via the respiratory tract, e.g., by inhalation, insufflation or nasal spray, or may be administered intraperitoneal, or to mucosal membranes. Suitable carriers are known to those skilled in the pharmaceutical area.

Preferably, the multicyclic spin trapping compound is provided in a composition with a suitable carrier, at a concentration which is effective to permit, after administration to a patient, the formation of a spin adduct of the compound and a free radical in the patient. The concentration of nitrone compound in the composition will depend on absorption, inactivation, excretion rates of the compound, and the condition of the patient, as well as other factors known to those skilled in the art. Using controlled release carriers, the dosage and release of the compound can be varied over time.

Multicyclic nitrone spin trapping compounds can be formulated in the appropriate carrier for the appropriate route of administration for treatment of a particular disease or disorder, including diseases or disorders of the central and peripheral nervous systems, and disorders arising from ischemia, infection, inflammation, oxidation from exposure to radiation or cytotoxic compounds, as well as due to naturally occurring processes such as aging.

The present invention will be further understood by reference to the following non-limiting examples.

Equipment and Materials

All EPR spectra were obtained on a Bruker E 300 or EXP 300E spectrometer equipped with 100 kHz field modulation at X-Band, at room temperature under nitrogen (unless otherwise indicated). Hyperfine splitting constants were derived form spectral measurements based on spectrometer calibrated field markers periodically checked with Fremy's salt. Computer simulations were conducted using a program based on the program of Dr. U. M. Oehler. Oehler and Janzen, *Can. J. Chem.*, 60:1542–1548 (1982).

NMR spectra were recorded on a Varian XL-300 spectrometer using $CDCl_3$ as solvent and tetramethylsilane (TMS) as an internal standard. Microanalysis (C,H,N) was performed by Galbraith Laboratories, Inc. (Knoxville, Tenn.). Mass spectra were obtained on a VG Quattro system.

Chemicals were purchased from Aldrich Chemical Co. and Fisher Scientific Co. and were used as received unless otherwise stated. Solvents were reagent grade unless otherwise indicated.

EXAMPLE 1

Synthesis of TRAZON

Sodium tungstate (2.64 g, 8 mmol) was placed into a 500-mL, three necked, round-bottomed flask equipped with a 100-mL pressure-equalizing dropping funnel, a thermometer, and a magnetic stirring bar. After the flask was flushed with nitrogen, water (40 mL) and 1,3,3-trimethyl-6-azabicyclo[3.2.1]octane (30.6 g, 200 mmol) were added. The flask was cooled with an ice-salt bath to –5° C. (internal temperature), and then 30% hydrogen peroxide (45 mL, 440 mmol) was added dropwise over a period of 1 hr to keep the internal temperature below 10° C.

After the addition was over, the cooling bath was removed and the reaction mixture was stirred for 3 hr at room temperature. The excess hydrogen peroxide was decomposed by adding sodium bisulphite (3 g) with ice cooling. The solution was then saturated with sodium chloride (25 g) and extracted with chloroform (5×100mL). The solvent was then removed on the rotavap under reduced pressure at room temperature. The thick yellow oil was then dissolved in 400 mL of distilled water and extracted with hexane (3×100 mL) to remove the unreacted amine and other impurities. The aqueous phase was then saturated with sodium chloride (75 g) and extracted with chloroform (5×100 mL). The combined extracts were dried over anhydrous sodium sulfate and the solvent was removed on the rotavap under reduced pressure at room temperature. The thick light colored oil (28.4 g, 85%) solidified on keeping in the freezer.

This material was then transferred to a sublimation apparatus and sublimed (bath temp.=40° C., 0.05 torr) to produce TRAZON as a colorless low melting crystalline solid (25 g, 75%). 1,3,3-trimethyl-6-azabicyclo[3.2.1]oct-6-ene-N-oxide ("TRAZON") was characterized as follows:

IR (thin film): $v_{max}$ 2950, 1562, 1467, 1395, 1238, 1191, 1180, 1153, 1120, 1099, 917, 885, 793 $cm^{-1}$.

$^1H$ NMR (300 MHz $CDCl_3$): δ6.60 (1H, s, H-7), 3.92 (1H, m, H-5), 2.17 (1H, m, $H-8_{anti}$), 2.03 (1H, br d, $H-8_{syn}$), 1.58 and 1.41 (2H, AB q, $J_{AB}$=12 Hz), 1.52 and 1.34 (2H, br AB q, $J_{AB}$=15 Hz), 1.90 (3H, s, C-1 methyl), 1.02 (6H, br s, C-3 methyls) ppm.

$^{13}C$ NMR (75 MHz, $CDCl_3$): δ139.7 (olefinic), 72.2 (C-5), 46.0, 45.2, 43.4 (C-1), 35.7, 35.5, 32.1, 30.1 (C-3), 22.8 ppm.

Mass: m/e 167 ($M^+$, 100%), 152 ($M^+$- methyl, 10%), 150 (25%), 137 ($M^+$- two methyls, 5%), 122 (M+- three methyls, 10%), 112 (10%), 111 (40%),110 (70%), 107 (15%), 98 (55%), 94 (50%), 91 (25%), 83 (10%), 82 (65%), 81 (80%), 80 (35%), 77 (30%), 67 (40%), 65 (20%), 56 (20%), 55 (60%), 53 (55%).

The C,H,N analysis is shown in Table 1 below:

TABLE 1

C, H, N Analysis
$C_{10}H_{17}NO$; Mol. Wt. = 167.

|  | calculated | found |
|---|---|---|
| Carbon: | 71.92 | 71.99 |
| Hydrogen: | 10.27 | 10.26 |
| Nitrogen: | 8.38 | 8.29 |

Highly pure TRAZON was obtained as indicated by EPR. The EPR spectrum showed only a clean but typical baseline trace.

EXAMPLE 2

Formation of TRAZON Spin Adducts 1,3,3-trimethyl-6-azabicyclo[3.2.1]oct-6-ene-N-oxide ("TRAZON") was reacted with a variety of radicals to form the TRAZON-free radical spin adduct. The EPR spectra of each of the radicals was obtained, and the hyperfine splitting constants of the adducts were determined. Eleven different radicals, hydroxyl, n-butoxyl, t-butyloxyl, hydroperoxyl, methyl, ethyl, phenyl, 2-cyanopropoxyl, methoxy, 1-hydroxyethyl, and 2-hydroxypropyl radical, were individually trapped using TRAZON. Each free radical adduct of TRAZON was readily detectable with a distinctive EPR signal.

The hydroxyl radical adduct of TRAZON was formed as described in U.S. Ser. No. 08/558,701, the disclosure of which is incorporated herein by reference. The hydroxyl radical adduct of TRAZON was produced using the hydroxyl radical generating system: 1% $H_2O_2$ in phosphate buffer followed by UV illumination.

The phenyl radical spin adduct of TRAZON was obtained by phenyl radical addition to TRAZON using phenylazontriphenylmethane ("PAT") as a room temperature thermal source of phenyl radicals in benzene, as described in Janzen and Evans, *J. Am. Chem. Soc.,* 97:205–206 (1975), the disclosure of which is incorporated herein by reference.

The n-butoxyl, t-butyloxyl, methoxy, hydroperoxyl, methyl, ethyl, 2-cyanopropoxyl, 1-hydroxyethyl, and 2-hydroxypropyl racial adducts were formed as described in Janzen, E. G. and Haire, D. L., *Advances in Free Radical Chemistry,* edited by D. D. Tanner, JAI Press Inc., Greenwich, Conn., USA Ch. 8, pp. 253–295 (1990), the disclosure of which is incorporated herein by reference.

EPR Spectra of Spin Adducts

The EPR spectra of each of the spin adducts was obtained. The TRAZON adducts formed, solvent(s) used, reagents, and hyperfine splitting constants for each adduct are listed in Table 2, in FIG. 3. The TRAZON spin adducts had very clear EPR spectra with distinctive signatures for the different radicals trapped. Computer simulated spectra were generated for the hydroxyl, t-butyloxyl, hydroperoxyl, methyl, ethyl, phenyl, 2-cyanopropoxyl, methoxy, 1-hydroxyethyl, and 2-hydroxypropyl radical adducts which supported the hyperfine splitting constants assigned to these spectra.

EXAMPLE 3

Measurement of Rate of Spin Trapping of TRAZON

The rate of spin trapping of TRAZON was evaluated. The second order spin trapping rate constant for TRAZON was determined and compared to that of DMPO. Equal concentrations of TRAZON and DMPO were exposed to hydroxyl radicals (from photolysis of $H_2O_2$) and the EPR spectra recorded. The composite EPR spectrum was computer simulated. Based on the relative areas of individual spectra (TRAZON=48.27%; DMPO=51.72%; error about ±5%), the rate constants for spin trapping hydroxyl radicals were approximately equal.

EXAMPLE 4

Synthesis of Phenyl-TRAZON

TRAZON is reacted with the Grignard reagent, phenylmagnesium bromide, to cause addition to the nitrone. The hydroxylamine formed after protonation with dilute acid then is oxidized with cupric acetate to form α-phenyl TRAZON.

Modifications and variations of the present invention will be obvious to those skilled in the art from the foregoing detailed description. Such modifications and variations are intended to come within the scope of the following claims.

What is claimed is:

1. A composition comprising a multicyclic nitrone free radical spin trapping compound in association with a pharmaceutically acceptable carrier for administration to a patient.

2. The composition of claim 1 comprising an effective amount of the compound to permit, after administration of the composition to a patient, the formation of a spin adduct of the compound and a free radical in the patient.

3. The composition of claim 1 wherein the pharmaceutically acceptable carrier is selected from the group consisting of carriers for intravenous administration, oral administration, mucosal administration, administration via the respiratory tract, subcutaneous administration, and topical administration.

4. A bicyclic nitrone free radical spin trapping compound of Formula I:

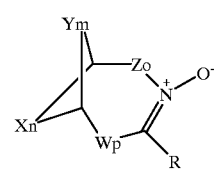

wherein

Xn is $(CH_2)n$ where n=1, 2 or 3; O; or N;

Ym is $(CH_2)m$ where m is 1, 2 or 3; O; or N;

Zo is $(CH_2)o$ where o is 0, 1, 2 or 3; or $C(CH_3)_2$;

Wp is $(CH_2)p$ where p is 0, 1, 2 or 3; and

R is H; $C_1$–$C_{12}$ alkyl; aryl; or pyrridine-N-oxide.

5. A composition comprising a multicyclic nitrone free radical spin trapping compound in association with a pharmaceutically acceptable carrier for administration to a patient wherein the multicyclic nitrone spin trapping compound is derived from a natural product.

6. A multicyclic nitrone spin trapping compound derived from a natural product selected from the group consisting of cocaine, codeine, and morphine.

7. A bicyclic nitrone spin trapping compound derived from a natural product selected from the group consisting of camphor, fenchone and norcamphor.

8. The bicyclic nitrone spin trapping compound of claim 7 wherein the compound is selected from the group consisting of

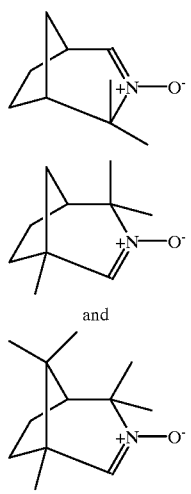

9. The bicyclic nitrone compound 1,3,3-trimethyl-6-azabicyclo [3.2.1]oct-6-ene-N-oxide.

10. A bicyclic nitrone spin trapping compound formed by reaction of the nitrone compound of claim 8 or 9 with a Grignard or organolithium reagent.

11. A composition comprising the compound of claim 9 in combination with a pharmaceutically acceptable carrier for administration to a patient.

12. The composition of claim 11 wherein the pharmaceutically acceptable carrier is selected from the group consisting of carriers for intravenous administration, oral administration, mucosal adminstration, administration via the respiratory tract, subcutaneous administration, and topical administration.

13. The compound of claim 9 wherein the compound is conjugated to a targeting molecule or a therapeutic molecule.

14. A free radical spin adduct of the compound of claim 4 or 9 and a free radical selected from the group consisting of hydroxyl, hydroperoxyl, phenyl, aryl, trichloromethyl, alkyl, alkoxyl, acylalkoxyl, sulfur, nitrogen, halogen, hydrogen and phosphorous centered radicals.

15. A method for detecting a free radical in a sample comprising:
reacting a sample comprising a free radical with a composition comprising a multicyclic nitrone spin trapping compound, to produce a spin adduct of the multicyclic nitrone spin trapping compound and the free radical; and
detecting the spin adduct, thereby to determine the presence of the free radical in the sample.

16. The method of claim 15 wherein the spin adduct is detected by electron paramagnetic resonance (EPR) spectroscopy.

17. The method of claim 16 wherein the free radical in the sample which is detected is selected from the group consisting of hydroxyl, hydroperoxyl, aryl, alkyl, alkoxyl and acyloxyl free radicals.

18. The method of claim 15 wherein the sample comprises a biological system.

19. The method of claim 15 wherein the method comprises administering a composition comprising the multicyclic nitrone spin trapping compound in a pharmaceutically acceptable carrier to a patient;
permitting the multicyclic nitrone spin trapping compound to react with a free radical in the patient to produce a spin adduct of multicyclic nitrone spin trapping compound and the radical; and
detecting the spin adduct, thereby to determine the presence of the radical in the patient.

20. The method of claim 19 wherein the composition is administered by a route selected from the group consisting of intravenous administration, oral administration, administration via the respiratory tract, subcutaneous administration, and topical administration, and comprises a pharmaceutically acceptable carrier for the route of administration.

21. A method for detecting a free radical in a sample comprising:
reacting a sample comprising a free radical with a composition comprising a multicyclic nitrone spin trapping compound, to produce a spin adduct of the multicyclic nitrone spin trapping compound and the free radical; and
detecting the spin adduct, thereby to determine the presence of the free radical in the sample, wherein the multicyclic nitrone spin trapping compound is derived from a natural product.

22. A method for detecting a free radical in a sample comprising:
reacting a sample comprising a free radical with a composition comprising a multicyclic nitrone spin trapping compound, to produce a spin adduct of the multicyclic nitrone spin trapping compound and the free radical; and
detecting the spin adduct, thereby to determine the presence of the free radical in the sample;
wherein the multicyclic nitrone spin trapping compound is 1,3,3-trimethyl-6-azabicyclo-[3.2.1]oct-6-ene-N-oxide.

* * * * *